(12) United States Patent
Mochizuki et al.

(10) Patent No.: US 10,300,191 B2
(45) Date of Patent: May 28, 2019

(54) BLOOD PURIFICATION APPARATUS

(71) Applicant: Nikkiso Company Limited, Tokyo (JP)

(72) Inventors: Hiroaki Mochizuki, Shizuoka (JP);
Harutoshi Okabe, Shizuoka (JP);
Sumiaki Matsuo, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 15/874,023

(22) Filed: Jan. 18, 2018

(65) Prior Publication Data
US 2018/0140766 A1 May 24, 2018

Related U.S. Application Data

(63) Continuation of application No. PCT/JP2016/071424, filed on Jul. 21, 2016.

(30) Foreign Application Priority Data

Jul. 23, 2015 (JP) .................................. 2015-145465

(51) Int. Cl.
*A61M 1/16* (2006.01)
*A61M 1/36* (2006.01)
*A61M 1/34* (2006.01)

(52) U.S. Cl.
CPC ............ *A61M 1/3646* (2014.02); *A61M 1/16* (2013.01); *A61M 1/1603* (2014.02);
(Continued)

(58) Field of Classification Search
CPC ............ B01D 2311/04; B01D 2311/10; B01D 2311/25; A61M 1/16; A61M 1/165;
(Continued)

(56) References Cited

U.S. PATENT DOCUMENTS

2007/0278155 A1* 12/2007 Lo ........................... A61M 1/16
210/646

FOREIGN PATENT DOCUMENTS

JP H01-201263 A 8/1989
JP 2002-113096 A 4/2002
(Continued)

OTHER PUBLICATIONS

English language machine translation of JP H01-201263, pp. 19, No Date.*

(Continued)

*Primary Examiner* — Pranav N Patel
(74) *Attorney, Agent, or Firm* — The Dobrusin Law Firm, PC (57) ABSTRACT

A blood purification apparatus comprising: a blood circuit including an arterial blood circuit and a venous blood circuit and that is capable of extracorporeally circulating blood of a patient from a distal end of the arterial blood circuit to a distal end of the venous blood circuit; a blood purification device provided between the arterial and the venous blood circuit of the blood circuit and that is capable of purifying the blood flowing in the blood circuit; a dialysate introduction line for introducing dialysate into the blood purification device and a dialysate drain line for discharging drain liquid from the blood purification device; a liquid delivery pump provided to the dialysate introduction line and that is capable of causing the dialysate in the dialysate introduction line to flow; a heating device that is capable of heating the dialysate to be introduced from the dialysate introduction line into the blood purification device; a temperature-detecting device that is capable of detecting a temperature of the dialysate heated by the heating device; and a control device that is capable of controlling at least the liquid delivery pump and the heating device, wherein the control device is configured (Continued)

so that, if a dialysate temperature detected by the temperature-detecting device is higher than or equal to a predetermined value, the liquid delivery pump is controlled to cause the dialysate in the heating device to flow to an upstream side or a downstream side with respect to the heating device without allowing the dialysate to be introduced into the blood purification device.

10 Claims, 7 Drawing Sheets

(52) U.S. Cl.
CPC ........ *A61M 1/1607* (2014.02); *A61M 1/1664* (2014.02); *A61M 1/1645* (2014.02); *A61M 1/34* (2013.01); *A61M 2205/3331* (2013.01); *A61M 2205/3368* (2013.01)

(58) Field of Classification Search
CPC .. A61M 1/1039; A61M 1/666; A61M 1/1662; A61M 1/1664; A61M 2205/3368; A61M 2205/3365; A61M 2205/3331
See application file for complete search history.

(56) References Cited

FOREIGN PATENT DOCUMENTS

| JP | 2012-034782 A | 2/2012 |
| WO | 2010/020390 A | 2/2010 |

OTHER PUBLICATIONS

English language machine translation of JP 2002-113096, pp. 27, No Date.*
International Search Report from the Japanese Patent Office for Application No. PCT/JP2016/071424 dated Sep. 6, 2016.

* cited by examiner

(*1) Start (S1) Liquid-delivering step (S2) Heating device h : activated
P2, P3, P4 : normal rotation (S3) t ≧ tmax (S4) Start overheating warning process

(S5) Heating device h : stop
P2, P3, P4 : stop
Opening-and-closing device 7 (L4:closed, L1:closed)

(S6) P2 : reverse rotation (S7) P2 : normal rotation (S8) t < tmax (S9) End overheating warning process

[Fig. 7]

(*1) Start (S1) Liquid-delivering step (S2) Heating device h : activated
P2, P3, P4 : normal rotation (S3) t ≧ tmax (S4) Start overheating warning process

(S5) Heating device h : stop
P2, P3, P4 : stop
Opening-and-closing device 7 (L4:closed, L1:open)

(S6) P2, P3 : reverse rotation (S7) P2, P3 : normal rotation (S8) t < tmax (S9) End overheating warning process

BLOOD PURIFICATION APPARATUS

FIELD

The present teachings relate to a blood purification apparatus for purifying the blood of a patient while extracorporeally circulating the blood.

BACKGROUND

A typical blood purification apparatus for giving dialysis treatment includes an arterial blood circuit and a venous blood circuit that form a blood circuit for extracorporeally circulating the blood of a patient, a blood purifier for purifying the blood that is extracorporeally circulated through the blood circuit, and an apparatus body provided with various treatment devices, such as a blood pump, for causing the blood circuit and the blood purifier to perform blood purification treatment. A vascular access catheter or puncture needles (an arterial puncture needle and a venous puncture needle) are attachable to the distal ends of the arterial blood circuit and the venous blood circuit.

When the blood pump is activated after the arterial puncture needle and the venous puncture needle, for example, are stuck into the patient, the blood of the patient flows through the arterial blood circuit and the venous blood circuit while being purified by the blood purifier. In the case of dialysis treatment, a dialysate introduction line for introducing dialysate into the blood purifier and a dialysate drain line for discharging drain liquid from the blood purifier are connected to the blood purifier.

Typically, the dialysate introduction line is provided with a heating device (a heater) for heating the dialysate to be introduced into the blood purifier to a predetermined temperature. The heating device is provided with a temperature-detecting device that is capable of detecting the temperature of the dialysate. The heating device is under feedback control in which the detected temperature is controlled to fall within a predetermined range. Since the dialysate to be introduced into the blood purifier is heated by the heating device, the temperature of the blood that is under extracorporeal circulation through the blood circuit can be prevented from dropping at the contact with the dialysate with blood purification membranes in the blood purifier interposed therebetween. Such a technique has not been disclosed by any publicly known invention, and there is no information on patent literature to be cited.

SUMMARY

The above known blood purification apparatus, however, has the following problems.

If the dialysate heated by the heating device is overheated and the temperature thereof exceeds the predetermined range, the heating of the dialysate and the delivery of the dialysate to the blood purifier need to be stopped until the temperature drops to a level within the predetermined range. However, even if the heating by the heating device is stopped, a heating portion has residual heat. Therefore, it takes a long time for the temperature of the dialysate to fall within the predetermined range.

Alternatively, a bypass line that allows the dialysate in the dialysate introduction line to bypass the blood purifier and to flow into the dialysate drain line may be provided. If the dialysate is overheated, the heating by the heating device is stopped and the dialysate is caused to flow into the bypass line so that the temperature of the dialysate can be lowered in a short time. In such a case, however, the bypass line and associated devices such as a valve for opening and closing the flow route are necessary. Consequently, the configuration of the apparatus becomes complicated, and the manufacturing cost increases.

The present teachings have been conceived in view of the above circumstances and provides a blood purification apparatus having a simple configuration while avoiding the increase in the manufacturing cost and in which the temperature of dialysate, if overheated, can be lowered in a shorter time and more easily.

According to the teachings herein, there is provided a blood purification apparatus including the following: a blood circuit including an arterial blood circuit and a venous blood circuit and that is capable of extracorporeally circulating blood of a patient from a distal end of the arterial blood circuit to a distal end of the venous blood circuit, a blood purification device provided between the arterial blood circuit and the venous blood circuit of the blood circuit and that is capable of purifying the blood flowing in the blood circuit, a dialysate introduction line for introducing dialysate into the blood purification device and a dialysate drain line for discharging drain liquid from the blood purification device, a liquid delivery pump provided to the dialysate introduction line and that is capable of causing the dialysate in the dialysate introduction line to flow, a heating device that is capable of heating the dialysate to be introduced from the dialysate introduction line into the blood purification device, a temperature-detecting device that is capable of detecting a temperature of the dialysate heated by the heating device, and a control device that is capable of controlling at least the liquid delivery pump and the heating device. The control device is configured such that, if a dialysate temperature detected by the temperature-detecting device is higher than or equal to a predetermined value, the liquid delivery pump is controlled to cause the dialysate in the heating device to flow to an upstream side or a downstream side with respect to the heating device without allowing the dialysate to be introduced into the blood purification device.

According to the teachings herein, in the blood purification apparatus taught herein, the liquid delivery pump is a peristaltic pump that is capable of undergoing normal rotation and reverse rotation. Furthermore, the control device is configured such that, if the dialysate temperature detected by the temperature-detecting device is higher than or equal to the predetermined value, the liquid delivery pump is controlled to cause the dialysate in the heating device to flow to an upstream portion of the dialysate introduction line by undergoing reverse rotation.

According to the teachings herein, in the blood purification apparatus taught herein, the dialysate introduction line is connected to a dialysate storage bag that stores the dialysate by a predetermined amount. Furthermore, the control device is configured such that, if the dialysate temperature detected by the temperature-detecting device is higher than or equal to the predetermined value, the liquid delivery pump is controlled to cause the dialysate in the heating device to flow into the dialysate storage bag.

According to the teachings herein, the blood purification apparatus taught herein further includes a flow route for introducing the dialysate heated by the heating device into the blood purification device or into the blood circuit, and an opening-and-closing device that is capable of opening and closing the flow route. Furthermore, the control device controls the opening-and-closing device to close the flow route if the dialysate temperature detected by the temperature-detecting device is higher than or equal to the predetermined value.

According to the teachings herein, the blood purification apparatus taught herein further includes an outside-air-introducing device that is capable of introducing, if the dialysate temperature detected by the temperature-detecting device is higher than or equal to the predetermined value, outside air into the dialysate introduction line in accordance with the dialysate that is caused to flow by the liquid delivery pump.

According to the teachings herein, in the blood purification apparatus taught herein, the outside-air-introducing device includes a valve device that is attached to an extension flow route extending from the dialysate introduction line and whose distal end is open to atmosphere, the valve device being capable of opening and closing the extension flow route. Furthermore, when the valve device is open, outside air is allowed to be introduced into the dialysate introduction line through the extension flow route.

According to the teachings herein, in the blood purification apparatus taught herein, the outside-air-introducing device includes a pump device that is attached to an extension flow route extending from the dialysate introduction line and whose distal end is open to atmosphere. Furthermore, when the pump device is activated, outside air is allowed to be introduced into the dialysate introduction line through the extension flow route.

According to the teachings herein, the blood purification apparatus taught herein further includes a filtration pump provided to the dialysate drain line and that is capable of causing the drain liquid in the dialysate drain line to flow. Furthermore, the control device is configured such that, if the dialysate temperature detected by the temperature-detecting device is higher than or equal to the predetermined value, the filtration pump is controlled to rotate at substantially the same flow rate and in the same direction as the liquid delivery pump.

According to the teachings herein, in the blood purification apparatus taught herein, the temperature-detecting device is provided to the heating device or to a flow route for introducing the dialysate heated by the heating device into the blood purification device or into the blood circuit.

According to the teachings herein, in the blood purification apparatus taught herein, the temperature-detecting device is provided to the heating device. Furthermore, the control device is configured such that, if the dialysate temperature detected by the temperature-detecting device is higher than or equal to the predetermined value, the temperature-detecting device is controlled to detect the temperature after the liquid delivery pump causes the dialysate in the heating device to flow to an outside of the heating device and after the liquid delivery pump returns the thus flowed dialysate to the heating device.

According to the teachings herein, in the blood purification apparatus taught herein, until the temperature detected by the temperature-detecting device becomes lower than the predetermined value, the control device repeatedly executes a step of causing the dialysate in the heating device to flow to the outside of the heating device and a step of returning the thus flowed dialysate to the heating device.

According to the teachings herein, the control device is configured such that, if the dialysate temperature detected by the temperature-detecting device is higher than or equal to the predetermined value, the liquid delivery pump is controlled to cause the dialysate in the heating device to flow to the upstream side or the downstream side with respect to the heating device without allowing the dialysate to be introduced into the blood purification device. Hence, the configuration of the apparatus can be simplified, and the increase in the manufacturing cost can be avoided. Furthermore, even if the dialysate is overheated, the temperature of the dialysate can be lowered in a shorter time and more easily.

According to the teachings herein, the liquid delivery pump is a peristaltic pump that is capable of undergoing normal rotation and reverse rotation. Furthermore, the control device is configured such that, if the dialysate temperature detected by the temperature-detecting device is higher than or equal to the predetermined value, the liquid delivery pump is controlled to cause the dialysate in the heating device to flow to the upstream portion of the dialysate introduction line by undergoing reverse rotation. Hence, the temperature of the dialysate can be lowered in a shorter time and more easily. Moreover, the overheated dialysate can be assuredly prevented from accidentally flowing into the blood purification device.

According to the teachings herein, the dialysate introduction line is connected to the dialysate storage bag that stores the dialysate by the predetermined amount. Furthermore, the control device is configured such that, if the dialysate temperature detected by the temperature-detecting device is higher than or equal to the predetermined value, the liquid delivery pump is controlled to cause the dialysate in the heating device to flow into the dialysate storage bag. Hence, the overheated dialysate is mixed with the dialysate in the dialysate storage bag. Therefore, the temperature of the dialysate can be lowered more efficiently.

According to the teachings herien, the blood purification apparatus further includes the flow route for introducing the dialysate heated by the heating device into the blood purification device or into the blood circuit, and the opening-and-closing device that is capable of opening and closing the flow route. Furthermore, the control device controls the opening-and-closing device to close the flow route if the dialysate temperature detected by the temperature-detecting device is higher than or equal to the predetermined value. Hence, the temperature of the dialysate can be lowered while the backward flow of the dialysate from the blood purification device is prevented.

According to the teachings herien, the blood purification apparatus further includes the outside-air-introducing device that is capable of introducing, if the dialysate temperature detected by the temperature-detecting device is higher than or equal to the predetermined value, outside air into the dialysate introduction line in accordance with the dialysate that is caused to flow by the liquid delivery pump. Hence, even if the flow route is closed by the opening-and-closing device, the dialysate in the heating device can be caused to flow to the outside of the heating device assuredly and smoothly.

According to the teachings herein, the outside-air-introducing device includes the valve device that is attached to the extension flow route extending from the dialysate introduction line and whose distal end is open to atmosphere, the valve device being capable of opening and closing the extension flow route. Furthermore, when the valve device is open, outside air is allowed to be introduced into the dialysate introduction line through the extension flow route. Hence, the outside air can be introduced into the dialysate introduction line with a simple configuration.

According to the teachings herein, the outside-air-introducing device includes the pump device that is attached to the extension flow route extending from the dialysate introduction line and whose distal end is open to atmosphere. Furthermore, when the pump device is activated, outside air is allowed to be introduced into the dialysate introduction line through the extension flow route. Hence, the flow rate of the outside air to be introduced into the dialysate introduction line can be adjusted as intended by controlling the driving of the pump device.

According to the teachings herein, the blood purification apparatus further includes the filtration pump provided to the dialysate drain line and that is capable of causing the drain liquid in the dialysate drain line to flow. Furthermore, the control device is configured such that, if the dialysate temperature detected by the temperature-detecting device is higher than or equal to the predetermined value, the filtration pump is controlled to rotate at substantially the same flow rate and in the same direction as the liquid delivery pump. Hence, the dialysate in the heating device can be caused to flow to the outside of the heating device by the liquid delivery pump with substantially no restrictions, compared with a case where the flow route provided as the dialysate introduction line is closed.

According to the teachings herein, the temperature-detecting device is provided to the heating device or to the flow route for introducing the dialysate heated by the heating device into the blood purification device or into the blood circuit. Hence, the temperature-detecting device can assuredly detect the temperature, and the temperature of the dialysate can be lowered while the backward flow of the dialysate from the blood purification device is prevented.

According to the teachings herein, the temperature-detecting device is provided to the heating device. Furthermore, the control device is configured such that, if the dialysate temperature detected by the temperature-detecting device is higher than or equal to the predetermined value, the temperature-detecting device is controlled to detect the temperature after the liquid delivery pump causes the dialysate in the heating device to flow to an outside of the heating device and after the liquid delivery pump returns the thus flowed dialysate to the heating device. Hence, the temperature of the dialysate can be lowered automatically.

According to the teachings herein, until the temperature detected by the temperature-detecting device becomes lower than the predetermined value, the control device repeatedly executes the step of causing the dialysate in the heating device to flow to the outside of the heating device and the step of returning the thus flowed dialysate to the heating device. Hence, the temperature of the dialysate can be lowered automatically and assuredly.

DETAILED DESCRIPTION

Embodiments of the present teachings are described specifically with reference to the drawings.

Figure 1:
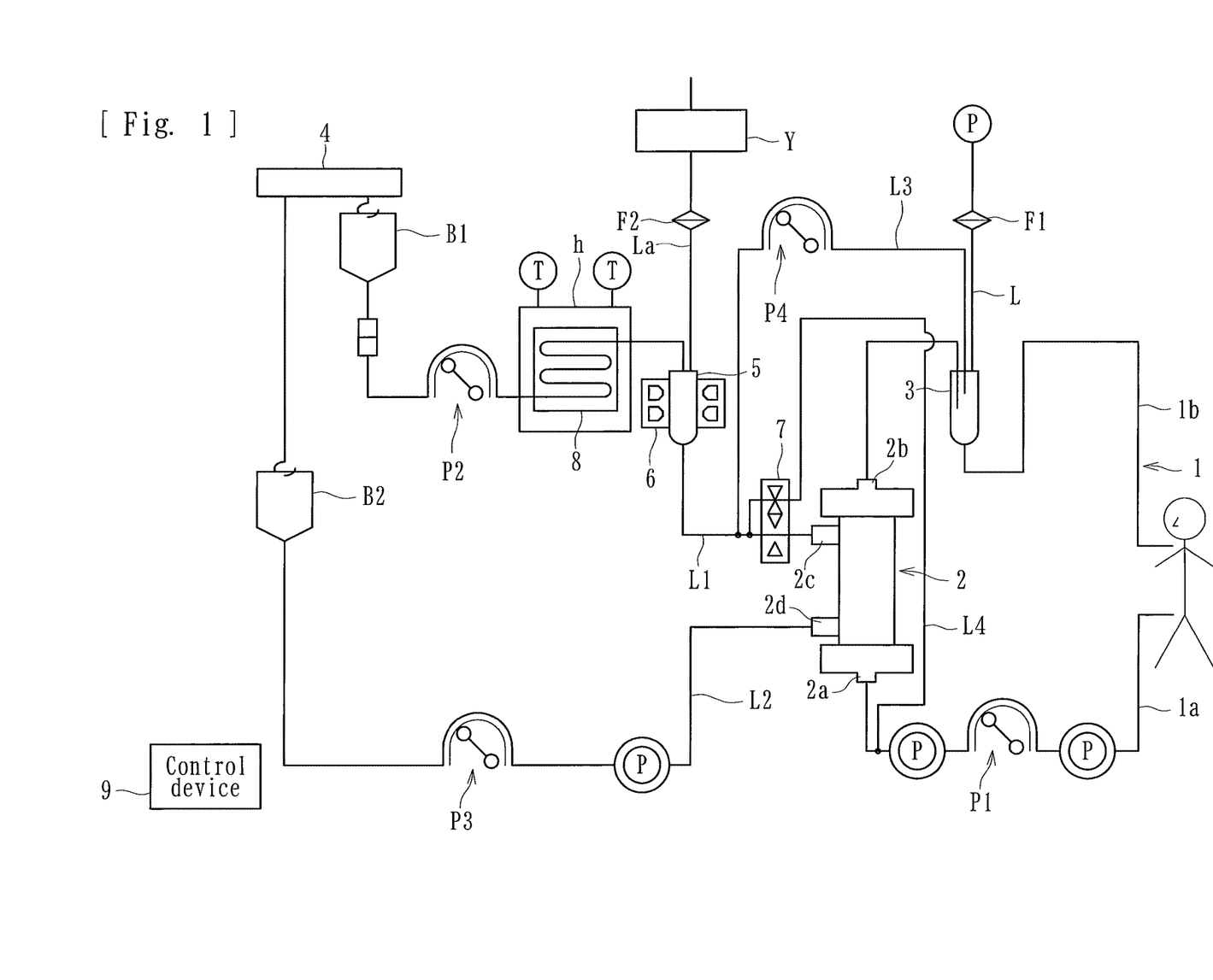
FIG. 1 is a schematic diagram of a blood purification apparatus according to a first embodiment of the present teachings.

A blood purification apparatus according to a first embodiment is applied to a hemodialysis apparatus for purifying the blood of a patient while extracorporeally circulating the blood. As illustrated in FIG. 1, the blood purification apparatus basically includes a blood circuit 1 including an arterial blood circuit 1a and a venous blood circuit 1b, a dialyzer 2 (a blood purification device) interposed between the arterial blood circuit 1a and the venous blood circuit 1b and that purifies the blood flowing in the blood circuit 1, a blood pump P1 in the form of a peristaltic pump provided to the arterial blood circuit 1a, a dialysate introduction line L1 and a dialysate drain line L2, a liquid delivery pump P2 and a filtration pump P3 provided to the dialysate introduction line L1 and the dialysate drain line L2, respectively, dialysate supply lines L3 and L4, a heating device h, a control device 9, and an outside-air-introducing device Y. Reference character P given in the drawing denotes a pressure-detecting device.

The arterial blood circuit 1a and the venous blood circuit 1b are provided at the distal ends thereof with connectors, respectively. An arterial puncture needle and a venous puncture needle (not illustrated) are connectable to the arterial blood circuit 1a and the venous blood circuit 1b with the connectors interposed therebetween, respectively. When the blood pump P1 is activated (to undergo normal rotation) with the arterial puncture needle at the distal end of the arterial blood circuit 1a and the venous puncture needle at the distal end of the venous blood circuit 1b being stuck in the patient, the blood of the patient flows through the arterial blood circuit 1a and reaches the dialyzer 2, where the blood is purified. Subsequently, the blood flows through the venous blood circuit 1b and returns into the body of the patient. Instead of sticking the arterial puncture needle and the venous puncture needle into a blood vessel of the patient, a double-lumen catheter may be inserted into the subclavian vein or the femoral vein of the patient or into a blood vessel of an arm of the patient, for example.

The venous blood circuit 1b is provided with an air-trap chamber 3 at a halfway position thereof. The blood that is extracorporeally circulated undergoes bubble removal in the air-trap chamber 3 and then returns into the patient. An air flow route L extends from the top of the air-trap chamber 3. The air flow route L is provided with a hydrophobic filter F1 at a halfway position thereof and a pressure-detecting device P at the distal end thereof. The pressure-detecting device P is capable of detecting the venous pressure.

The dialyzer 2 has, in a housing thereof, a blood inlet 2a (a blood introduction port), a blood outlet 2b (a blood delivery port), a dialysate inlet 2c (an inlet of the dialysate flow route, or a dialysate introduction port), and a dialysate outlet 2d (an outlet of the dialysate flow route, or a dialysate delivery port). The proximal end of the arterial blood circuit 1a is connected to the blood inlet 2a. The proximal end of the venous blood circuit 1b is connected to the blood outlet 2b. The dialysate inlet 2c and the dialysate outlet 2d are connected to the dialysate introduction line L1 and the dialysate drain line L2, respectively.

The dialyzer 2 houses a plurality of hollow fiber membranes (not illustrated), and such hollow fibers serve as blood purification membranes for purifying the blood. The blood purification membranes in the dialyzer 2 define blood flow routes (each extending between the blood inlet 2a and the blood outlet 2b) in which the blood of the patient flows and dialysate flow routes (each extending between the dialysate inlet 2c and the dialysate outlet 2d) in which the dialysate flows. The hollow fiber membranes serving as the blood purification membranes each have a number of very small holes (pores) extending therethrough from the outer peripheral surface to the inner peripheral surface. Hence, impurities and the like contained in the blood are allowed to penetrate through the membranes into the dialysate.

The dialysate introduction line L1 provides a flow route for introducing the dialysate into the dialyzer 2 and has one end thereof connected to the dialysate inlet 2c of the dialyzer 2. The dialysate introduction line L1 is provided with the liquid delivery pump P2 in the form of a peristaltic pump that delivers liquid by squeezing a flexible tube forming the flow route provided as the dialysate introduction line L1. The other end of the dialysate introduction line L1 is connected to a dialysate storage bag B1 that stores a predetermined amount of dialysate. When the liquid delivery pump P2 is activated (to undergo normal rotation), the dialysate in the dialysate storage bag B1 can be introduced into the dialyzer 2.

The dialysate drain line L2 provides a flow route for discharging drain liquid from the dialyzer 2 and has one end thereof connected to the dialysate outlet 2d of the dialyzer 2. The dialysate drain line L2 is provided with the filtration pump P3 in the form of a peristaltic pump that delivers liquid by squeezing a flexible tube forming the flow route provided as the dialysate drain line L2. The other end of the dialysate drain line L2 is connected to a drain-liquid storage bag B2 that stores a predetermined amount of drain liquid. When the filtration pump P3 is activated (to undergo normal rotation), the dialysate (the drain liquid) discharged from the dialyzer 2 can be introduced into the drain-liquid storage bag B2.

With the normal rotation of the liquid delivery pump P2, the dialysate in the dialysate storage bag B1 flows toward the dialyzer 2. With the normal rotation of the filtration pump P3, the dialysate (the drain liquid) in the dialyzer 2 flows toward the drain-liquid storage bag B2. The dialysate storage bag B1 and the drain-liquid storage bag B2 are hung on respective hooks provided to a weighing machine 4. The weighing machine 4 is capable of measuring in real time the weight of the dialysate storage bag B1 and the drain-liquid storage bag B2 (the total weight of the dialysate storage bag B1 and the drain-liquid storage bag B2). The dialysate storage bag B1 and the drain-liquid storage bag B2 are each a flexible storage case. Before the blood purification treatment is started, the drain-liquid storage bag B2 is empty with no drain liquid stored thereinside.

On the basis of the weight measured by the weighing machine 4 and preset values stored in advance, the driving of the blood pump P1, the liquid delivery pump P2, the filtration pump P3, and a peristaltic pump P4 is controlled. If there is a treatment condition that ultrafiltration is not to be performed for the patient, the driving speed of the filtration pump P3 is controlled to be the same as the driving speed of the liquid delivery pump P2. If ultrafiltration is to be performed, the driving speed of the filtration pump P3 is controlled to be higher than the driving speed of the liquid delivery pump P2 by the flow rate for ultrafiltration. If there is a difference, after a predetermined period of time, between the weight of the dialysate storage bag B1 and the drain-liquid storage bag B2 that is detected by the weighing machine 4 and the theoretical weight, the driving speed of the filtration pump P3 can be finely adjusted automatically so that correction for eliminating the difference is performed.

The dialysate supply line L3 provides a flow route branching off from a position of the dialysate introduction line L1 that is on the downstream side with respect to (nearer to the dialyzer 2 than) the liquid delivery pump P2, the flow route being connected to the air-trap chamber 3 provided to the venous blood circuit 1b. The dialysate supply line L3 is provided with the peristaltic pump P4 at a halfway position thereof. The peristaltic pump P4 is a pump that delivers liquid by squeezing a flexible tube forming the dialysate supply line L3. When the peristaltic pump P4 is activated to undergo normal rotation, the dialysate in the dialysate introduction line L1 can be supplied into the venous blood circuit 1b for substitution (post-substitution).

The dialysate supply line L4 provides a flow route branching off from a position of the dialysate introduction line L1 that is on the downstream side with respect to the liquid delivery pump P2 and on the downstream side with respect to (nearer to the dialyzer 2 than) the connection to the dialysate supply line L3, the flow route being connected to a predetermined position of the arterial blood circuit 1a (between the blood pump P1 and the dialyzer 2). The dialysate supply line L4 is provided with an opening-and-closing device 7 at a halfway position thereof. The opening-and-closing device 7 is an on-off valve that is capable of selectively closing and opening the dialysate introduction line L1 and the dialysate supply line L4. When the dialysate supply line L4 is open, the dialysate in the dialysate introduction line L1 can be supplied into the arterial blood circuit la for substitution (pre-substitution).

The dialysate introduction line L1 is further provided with an air-trap chamber 5 at a predetermined position thereof (on the downstream side with respect to the heating device h). In the air-trap chamber 5, bubbles contained in the dialysate to be introduced into the dialyzer 2 can be removed. Reference numeral 6 given in the drawing denotes a liquid-surface-detecting sensor for detecting the liquid surface in the air-trap chamber 5. An extension flow route La extends from the top of the air-trap chamber 5. The extension flow route La is provided with the outside-air-introducing device Y (to be described in detail below) and a hydrophobic filter F2.

Figure 2:
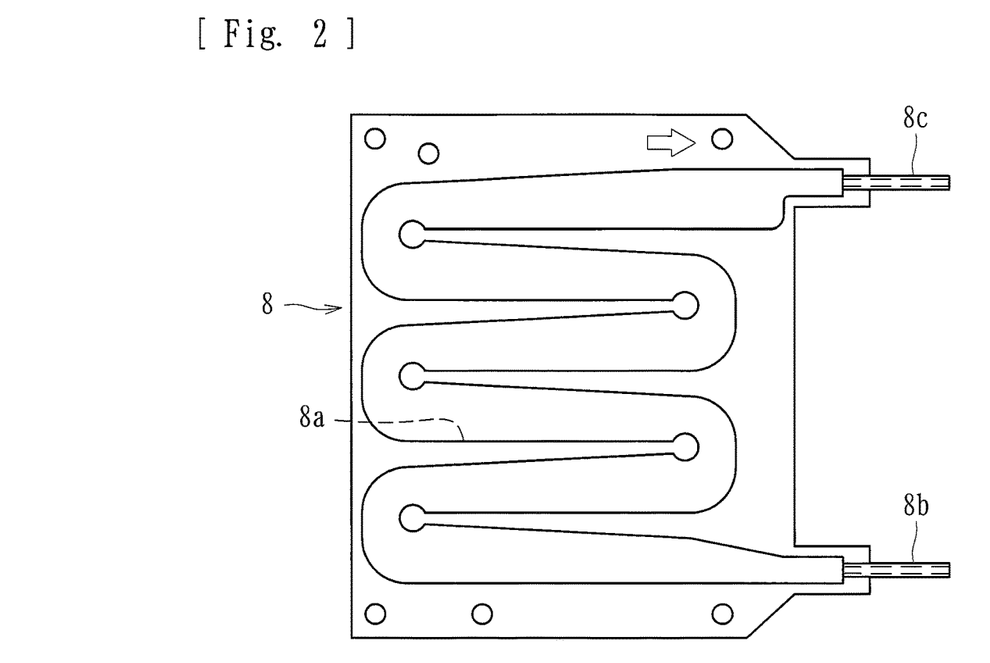
FIG. 2 is a schematic view of a heating bag applied to the blood purification apparatus.

The heating device h is provided to the dialysate introduction line L1 and is a heater that is capable of heating the dialysate to be introduced from the dialysate introduction line L1 into the dialyzer 2. A heating bag 8 illustrated in FIG. 2 is attachable to the heating device h. The heating bag 8 is formed of, for example, two flexible sheets that are joined and welded to each other, whereby a flow route 8a is provided. The flow route 8a has connecting portions 8b and 8c at two respective ends thereof. The connecting portions 8b and 8c are each connectable to the dialysate introduction line L1.

Figure 3:
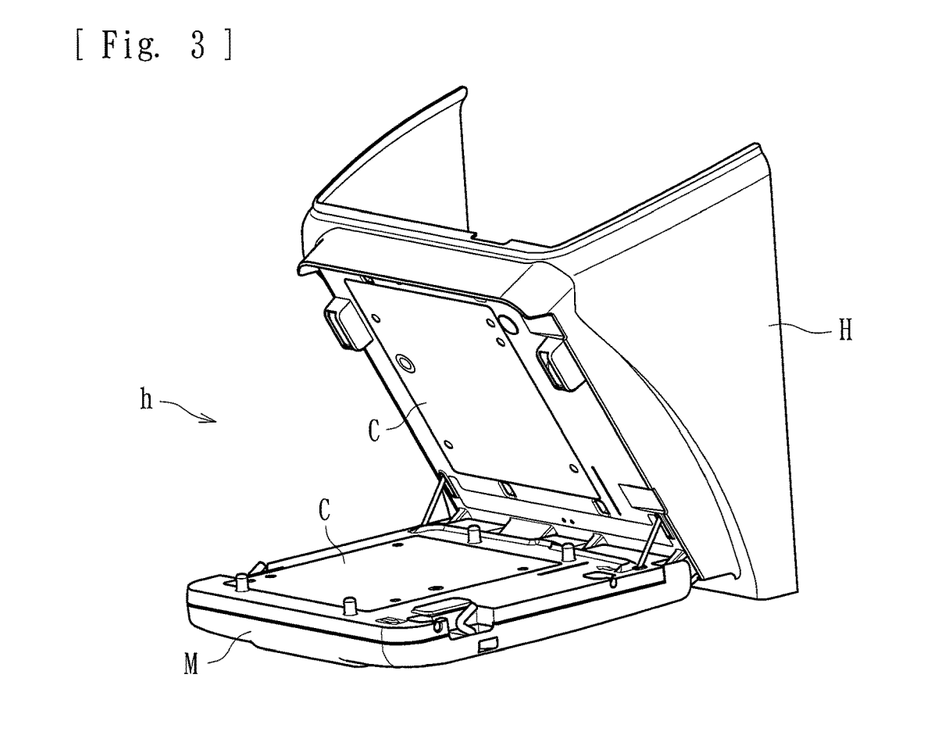
FIG. 3 is a perspective view of a heating device (with a lid thereof open) included in the blood purification apparatus.
Figure 4:
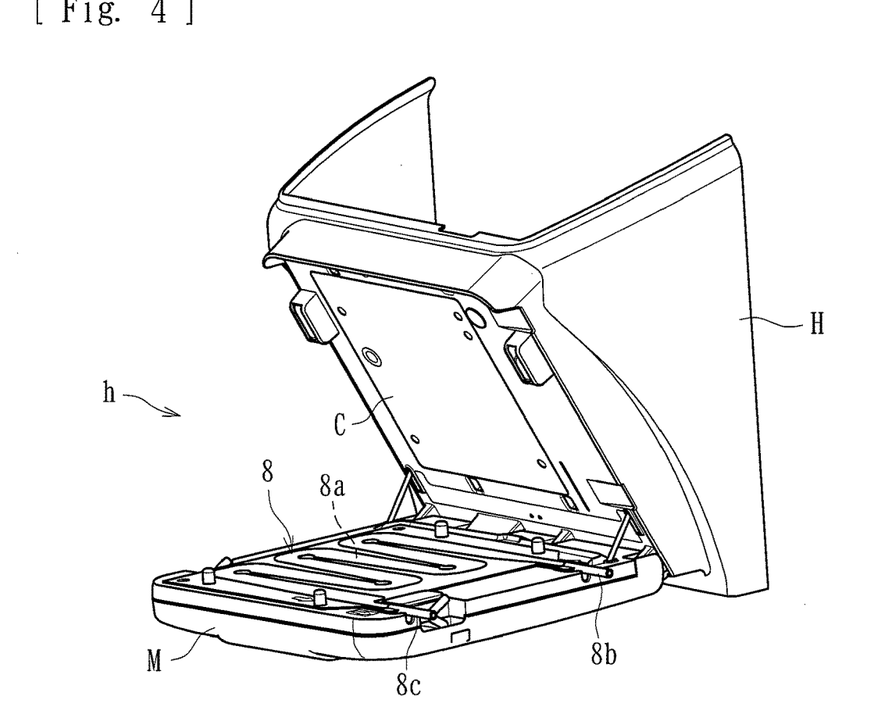
FIG. 4 is a perspective view of the heating device with the heating bag attached thereto.
Figure 5:
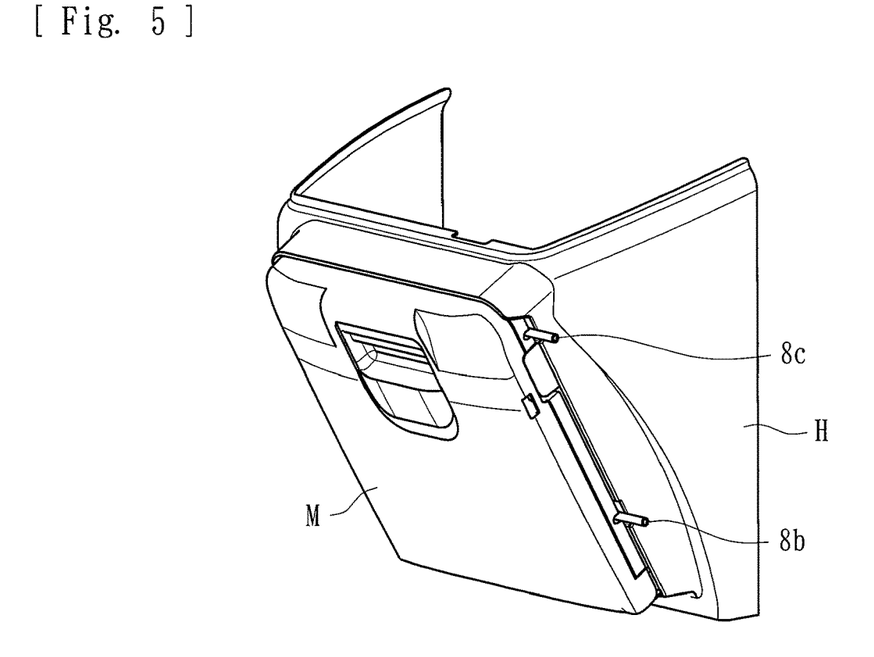
FIG. 5 is a perspective view of the heating device with the heating bag attached thereto and the lid thereof closed.

As illustrated in FIG. 3, the heating device h according to the first embodiment is provided to a housing portion H that is attached to a dialysis-apparatus body. The heating device h includes a lid portion M, and heating portions C provided to the housing portion H and the lid portion M, respectively. The heating portions C are each a metal plate member and are each capable of transmitting heat generated by a non-illustrated heat source (such as a heating wire). As illustrated in FIG. 4, the heating bag 8 is attached to the heating portion C provided to the lid portion M. Then, the lid portion M is closed as illustrated in FIG. 5. Thus, the heating bag 8 is held between the heating portions C provided to the housing portion H and the lid portion M, whereby the dialysate flowing in the flow route 8a can be heated with the heat generated by the heat sources.

The heating device h according to the first embodiment is also provided with temperature-detecting devices T (temperature sensors) that are capable of detecting the temperature of the dialysate heated by the heating device h. Thus, the feedback control of making the dialysate temperature fall within a predetermined range can be performed by the control device 9. The control device 9 is a microcomputer or the like included in the blood purification apparatus. The control device 9 is not only capable of performing feedback control of making the dialysate temperature fall within the predetermined range but also capable of controlling at least the liquid delivery pump P2 and the heating device h.

The control device 9 according to the first embodiment is configured such that, if the dialysate temperature detected by the temperature-detecting devices T is higher than or equal to a predetermined value (higher than or equal to a temperature at which the dialysate is regarded as being overheated), the introduction of the dialysate into the dialyzer 2 is stopped (the dialysate is not introduced into the blood purification device) and the liquid delivery pump P2 is controlled to cause the dialysate in the heating device h to flow to the outside of the heating device h. Specifically, if the dialysate temperature detected by the temperature-detecting devices T is higher than or equal to a predetermined value, the liquid delivery pump P2 is driven at a predetermined flow rate or for a predetermined period of time, whereby the dialysate in the flow route 8a of the heating bag 8 is caused to flow to a portion of the dialysate introduction line L1 that is on the outside of the heating device h. Thus, the configuration of the apparatus can be simplified, and the increase in the manufacturing cost can be avoided. Furthermore, even if the dialysate is overheated, the temperature of the dialysate can be lowered in a shorter time and more easily.

In particular, the liquid delivery pump P2 (as well as the filtration pump P3) according to the first embodiment is a peristaltic pump that is capable of undergoing normal rotation and reverse rotation. If the dialysate temperature detected by the temperature-detecting devices T is higher than or equal to the predetermined value, the control device 9 causes the liquid delivery pump P2 to undergo reverse rotation so that the dialysate in the heating device h can flow to an upstream portion of the dialysate introduction line L1 (specifically, the dialysate in the flow route 8a of the heating bag 8 is caused to flow into a portion of the dialysate introduction line L1 that is on the upstream side with respect to (nearer to the dialysate storage bag B1 than) the heating bag 8). Therefore, the overheated dialysate can be brought into contact with the upstream portion of the dialysate introduction line that has been in contact with the dialysate yet to be heated. Consequently, the temperature of the dialysate can be lowered in a shorter time and more easily. Moreover, the overheated dialysate can be assuredly prevented from accidentally flowing into the dialyzer 2 (in the first embodiment, into the dialyzer 2 and into the blood circuit 1).

Therefore, the control device 9 may alternatively be configured such that, if the dialysate temperature detected by the temperature-detecting devices T is higher than or equal to the predetermined value, the liquid delivery pump P2 is controlled to cause the dialysate in the heating device h to flow into the dialysate storage bag B1. In such a case, the overheated dialysate is mixed with the dialysate in the dialysate storage bag B1 (the dialysate that is yet to be heated by the heating device h). Therefore, the temperature of the dialysate can be lowered more efficiently.

As described above, the first embodiment employs the opening-and-closing device 7 that is capable of opening and closing the flow routes (the dialysate introduction line L1 and the dialysate supply line L4) for introducing the dialysate heated by the heating device h into the dialyzer 2 and into the blood circuit 1 (the arterial blood circuit 1a), respectively. Furthermore, the control device 9 causes the opening-and-closing device 7 to close the flow routes if the dialysate temperature detected by the temperature-detecting devices T is higher than or equal to the predetermined value. Hence, the temperature of the dialysate can be lowered while the backward flow of the dialysate from the dialyzer 2 is prevented.

Furthermore, as described above, the first embodiment employs the outside-air-introducing device Y. Furthermore, if the dialysate temperature detected by the temperature-detecting devices T is higher than or equal to the predetermined value, the outside-air-introducing device Y allows the outside air to be introduced into the dialysate introduction line L1 in accordance with the dialysate that is caused to flow by the liquid delivery pump P2. Hence, even if the flow route is closed by the opening-and-closing device 7, the dialysate in the heating device h can be caused to flow to the outside of the heating device h assuredly and smoothly. With the introduction of the outside air by the outside-air-introducing device Y, even if the heating bag 8 is replaced with a non-flexible tube, the dialysate in the heating device h can be caused to flow to the outside of the heating device h assuredly and smoothly.

The outside-air-introducing device Y according to the first embodiment is attached to the extension flow route La extending from the dialysate introduction line L1 and whose distal end is open to the atmosphere. The outside-air-introducing device Y is a valve device (such as an electromagnetic valve) that is capable of opening and closing the flow route provided as the extension flow route La. When the valve device is opened, the outside air can be introduced into the dialysate introduction line L1 through the extension flow route La. Thus, the outside air can be introduced into the dialysate introduction line L1 with a simple configuration.

In the first embodiment, the temperature-detecting devices T are provided to the heating device h. Furthermore, the control device 9 is configured such that, if the dialysate temperature detected by the temperature-detecting devices T is higher than or equal to the predetermined value, the liquid delivery pump P2 is controlled to cause the dialysate in the heating device h to flow to the outside of the heating device h (in the first embodiment, toward the dialysate storage bag B1 provided on the upstream side of the heating device h) and then to cause the thus flowed dialysate to return to the heating device h, where the temperature of the dialysate is detected by the temperature-detecting devices T. Hence, the temperature of the dialysate can be lowered automatically.

In particular, according to the first embodiment, the process of causing the dialysate in the heating device h to flow to the outside of the heating device h (in the first embodiment, toward the dialysate storage bag B1 provided on the upstream side of the heating device h) and the process of returning the thus flowed dialysate to the heating device h are repeatedly executed by the control device 9 until the temperature detected by the temperature-detecting devices T becomes lower than the predetermined value. Hence, the temperature of the dialysate can be lowered automatically and assuredly. The temperature-detecting devices T are preferably provided to the heating device h or to the flow route for introducing the dialysate heated by the heating device h into the dialyzer 2 (the blood purification device) or into the blood circuit 1. Thus, the temperature-detecting devices T can assuredly detect the temperature, and the temperature of the dialysate can be lowered while the backward flow of the dialysate from the dialyzer 2 (the blood purification device) is prevented.

Figure 6:
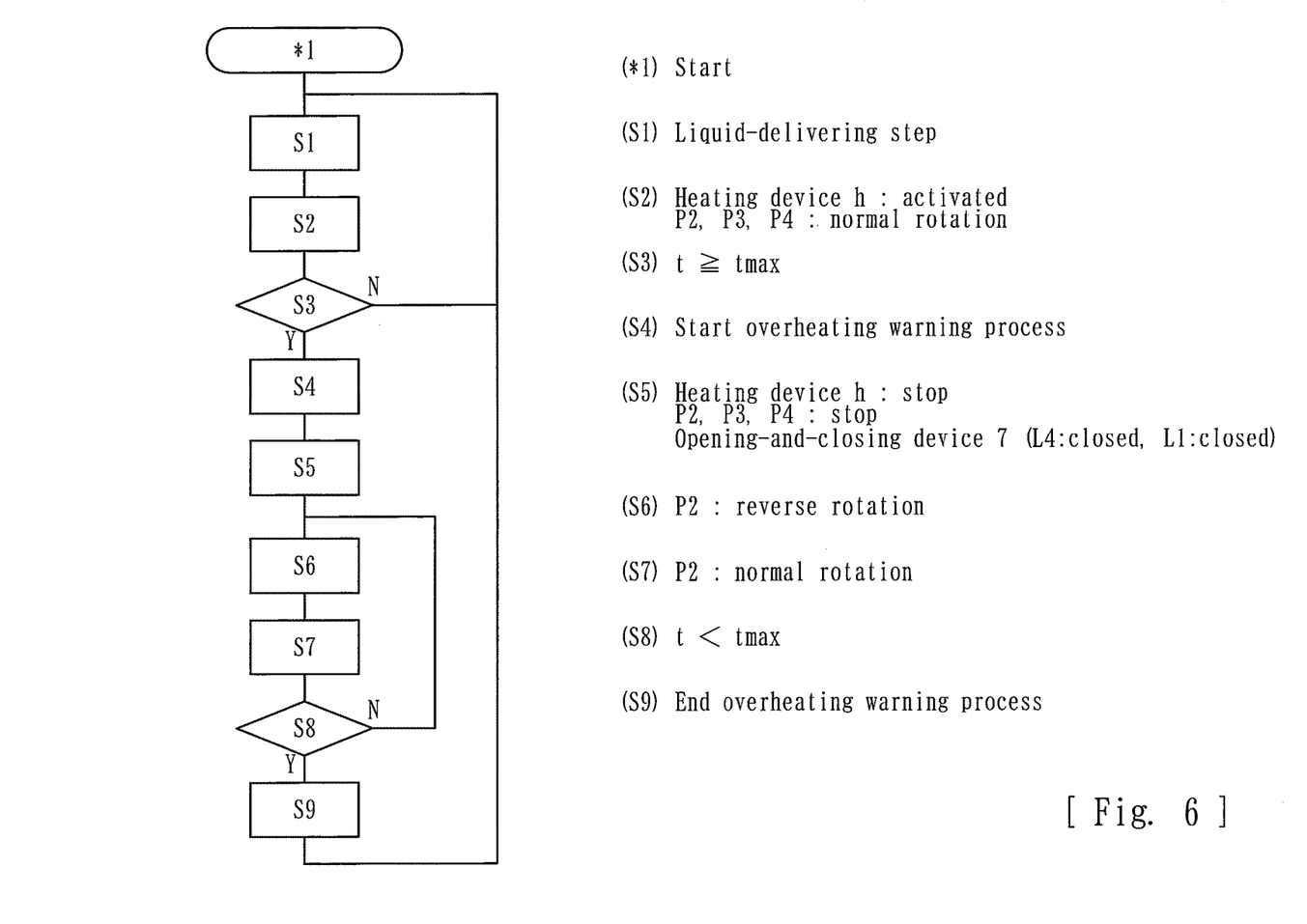
FIG. 6 is a flow chart of a control process executed by a control device included in the blood purification apparatus.

Now, the control process executed by the control device 9 according to the first embodiment will be described with reference to the flow chart illustrated in FIG. 6.

When a liquid-delivering step S1 of delivering the dialysate to the dialyzer 2 is started, the heating device h is activated and the liquid delivery pump P2, the filtration pump P3, and the peristaltic pump P4 are caused to undergo normal rotation in step S2. Subsequently, whether or not a dialysate temperature t detected by the temperature-detecting devices T is higher than or equal to a predetermined temperature tmax (the predetermined value) is checked (in step S3). If the dialysate temperature t is lower than the predetermined temperature tmax, the liquid-delivering step S1 is continued.

If the dialysate temperature t detected by the temperature-detecting devices T is higher than or equal to the predetermined temperature tmax, the process proceeds to step S4, where an overheating warning process is started. Then, in step S5, the heating by the heating device h is stopped (the operation of the heat source is stopped), and the liquid delivery pump P2, the filtration pump P3, and the peristaltic pump P4 are also stopped. In this step, the opening-and-closing device 7 closes the dialysate supply line L4 and the flow route of the dialysate introduction line L1 that is on the side nearer to the dialyzer 2 than the heating device h. Since the peristaltic pump P4 is stopped, the dialysate supply line L3 is also closed. Thus, the introduction of the dialysate into the dialyzer 2 is stopped.

Subsequently, in step S6, the liquid delivery pump P2 is caused to undergo reverse rotation at a predetermined flow rate or for a predetermined period of time, whereby the dialysate in the heating device h (the dialysate in the flow route 8a of the heating bag 8) is caused to flow to the outside of the heating device h and toward the dialysate storage bag B1. In this step, the dialysate in the heating device h only needs to reach the upstream portion of the dialysate introduction line L1. Preferably, the dialysate is caused to flow into the dialysate storage bag B1. In step S6, the valve device serving as the outside-air-introducing device Y is preferably opened so that the outside air can be introduced into the dialysate introduction line L1 in accordance with the dialysate that is caused to flow by the liquid delivery pump.

After the liquid delivery pump P2 is caused to undergo reverse rotation at a predetermined flow rate or for a predetermined period of time in step S6, the liquid delivery pump P2 is caused to undergo normal rotation in step S7, whereby the dialysate caused to flow in step S6 is returned into the heating device h (into the flow route 8a of the heating bag 8). Then, whether or not the dialysate temperature t detected by the temperature-detecting devices T is lower than the predetermined temperature tmax (the predetermined value) is checked (in step S8). If the dialysate temperature t is higher than or equal to the predetermined temperature tmax, the process returns to step S6, where the liquid delivery pump P2 is caused to undergo reverse rotation at a predetermined flow rate or for a predetermined period of time. Then, steps S7 and S8 are performed again.

If the dialysate temperature t detected by the temperature-detecting devices T is lower than the predetermined temperature tmax, the process proceeds to step S9, where the overheating warning process is ended. Then, the control process is repeated from step S1.

Instead of the above control process, if the dialysate temperature detected by the temperature-detecting devices T is higher than or equal to the predetermined value, the control device 9 may cause the filtration pump P3 to rotate at substantially the same flow rate and in the same direction as the liquid delivery pump P2. Such a control process executed by the control device 9 will now be described with reference to the flow chart illustrated in FIG. 7.

Figure 7:
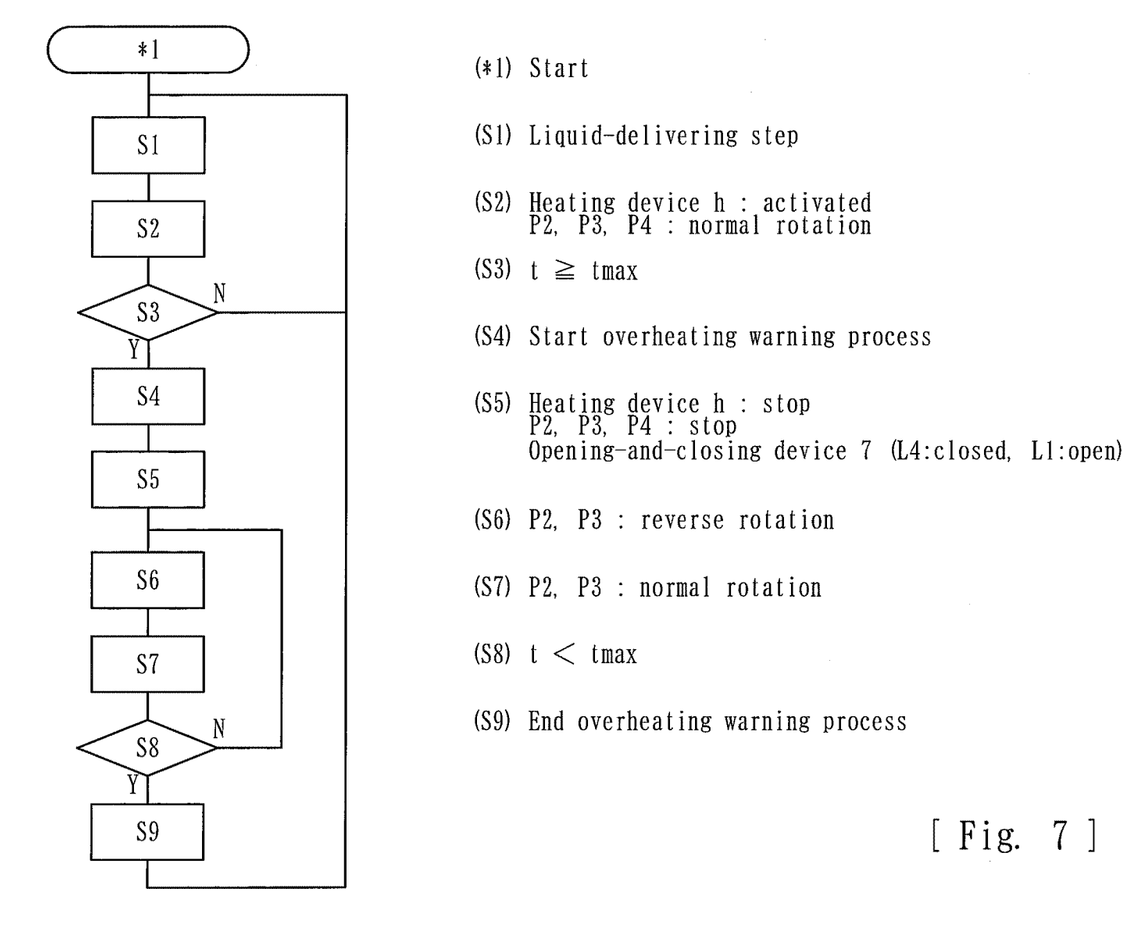
FIG. 7 is a flow chart of another control process executed by the control device included in the blood purification apparatus.

When a liquid-delivering step S1 of delivering the dialysate to the dialyzer 2 is started, the heating device h is activated and the liquid delivery pump P2, the filtration pump P3, and the peristaltic pump P4 are caused to undergo normal rotation in step S2. Subsequently, whether or not the dialysate temperature t detected by the temperature-detecting devices T is higher than or equal to a predetermined temperature tmax (the predetermined value) is checked (in step S3). If the dialysate temperature t is lower than the predetermined temperature tmax, the liquid-delivering step S1 is continued.

If the dialysate temperature t detected by the temperature-detecting devices T is higher than or equal to the predetermined temperature tmax, the process proceeds to step S4, where an overheating warning process is started. Then, in step S5, the heating by the heating device h is stopped (the operation of the heat source is stopped), and the liquid delivery pump P2, the filtration pump P3, and the peristaltic pump P4 are also stopped. In this step, the opening-and-closing device 7 closes the dialysate supply line L4 but opens the flow route of the dialysate introduction line L1 that is on the side nearer to the dialyzer 2 than the heating device h. Since the peristaltic pump P4 is stopped, the dialysate supply line L3 is also closed. Thus, the introduction of the dialysate into the dialyzer 2 is stopped.

Subsequently, in step S6, the liquid delivery pump P2 and the filtration pump P3 are caused to undergo reverse rotation at a predetermined flow rate or for a predetermined period of time (rotated at substantially the same flow rate and in the same direction), whereby the dialysate in the heating device h (the dialysate in the flow route 8a of the heating bag 8) is caused to flow to the outside of the heating device h and toward the dialysate storage bag B1. In this step, the dialysate in the heating device h only needs to reach the upstream portion of the dialysate introduction line L1. Preferably, the dialysate is caused to flow into the dialysate storage bag B1.

After the liquid delivery pump P2 and the filtration pump P3 are caused to undergo reverse rotation at a predetermined flow rate or for a predetermined period of time in step S6, the liquid delivery pump P2 and the filtration pump P3 are caused to undergo normal rotation (rotated at substantially the same flow rate and in the same direction) in step S7, whereby the dialysate caused to flow in step S6 is returned into the heating device h (into the flow route 8a of the heating bag 8). Then, whether or not the dialysate temperature t detected by the temperature-detecting devices T is lower than the predetermined temperature tmax (the predetermined value) is checked (in step S8). If the dialysate temperature t is higher than or equal to the predetermined temperature tmax, the process returns to step S6, where the liquid delivery pump P2 and the filtration pump P3 are caused to undergo reverse rotation at a predetermined flow rate or for a predetermined period of time. Then, steps S7 and S8 are performed again. If the dialysate temperature t detected by the temperature-detecting devices T is lower than the predetermined temperature tmax, the process proceeds to step S9, where the overheating warning process is ended. Then, the control process is repeated from step S1.

As described above, if the dialysate temperature detected by the temperature-detecting devices T is higher than or equal to a predetermined value, the control device 9 causes the filtration pump P3 to rotate at substantially the same flow rate and in the same direction as the liquid delivery pump P2. Thus, the dialysate in the heating device h can be caused to flow to the outside of the heating device h by the liquid delivery pump P2 with substantially no restrictions, compared with a case where the flow route provided as the dialysate introduction line L1 is closed.

Now, a blood purification apparatus according to a second embodiment of the present teachings will be described.

Figure 8:
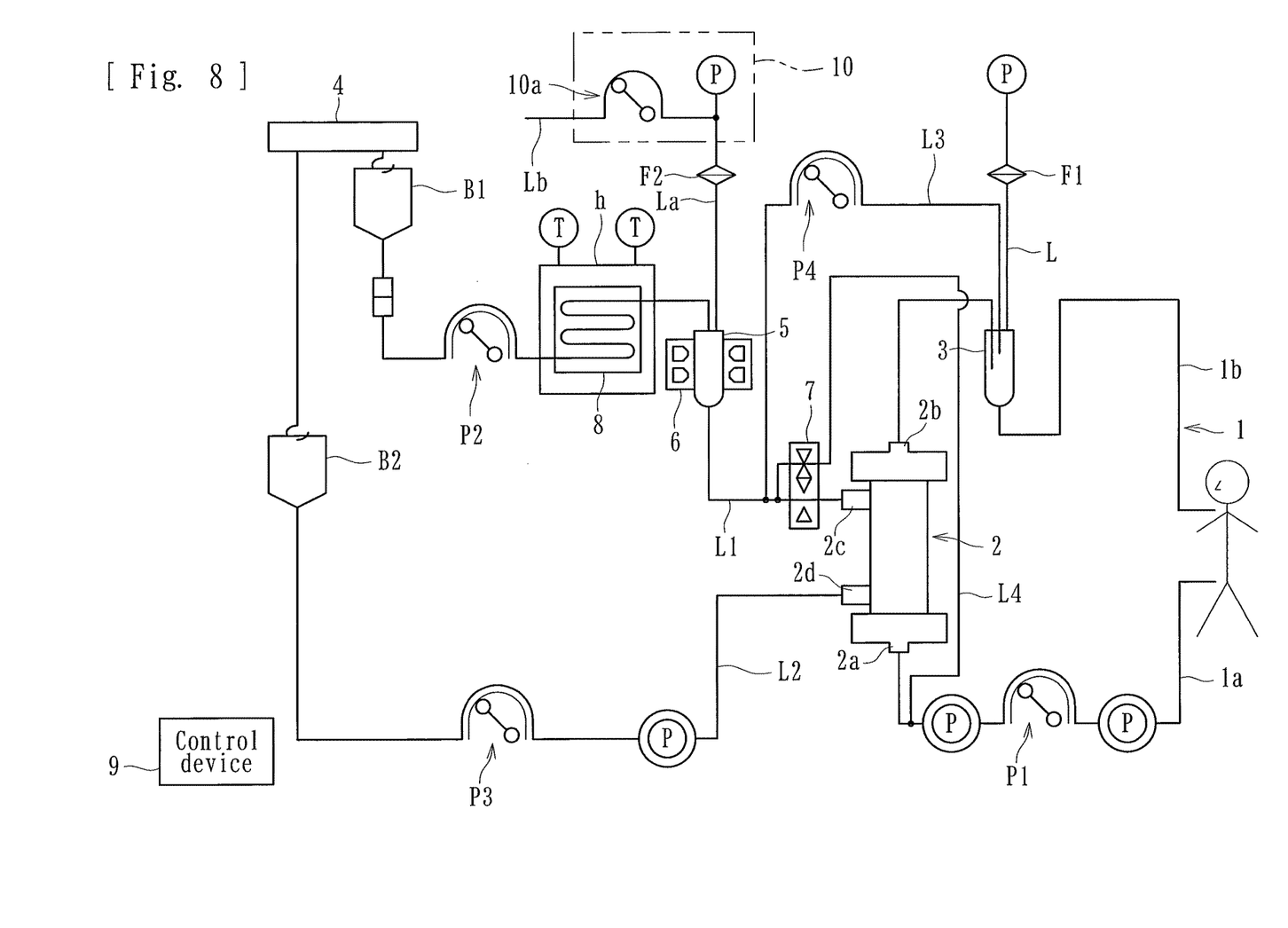
FIG. 8 is a schematic diagram of a blood purification apparatus according to a second embodiment of the present teachings.

As with the case of the first embodiment, a blood purification apparatus according to the second embodiment is applied to a hemodialysis apparatus for purifying the blood of a patient while extracorporeally circulating the blood. As illustrated in FIG. 8, the blood purification apparatus basically includes a blood circuit 1 including an arterial blood circuit 1a and a venous blood circuit 1b, a dialyzer 2 (a blood purification device) interposed between the arterial blood circuit 1a and the venous blood circuit 1b and that purifies the blood flowing in the blood circuit 1, a blood pump P1 in the form of a peristaltic pump provided to the arterial blood circuit 1a, a dialysate introduction line L1 and a dialysate drain line L2, a liquid delivery pump P2 and a filtration pump P3 provided to the dialysate introduction line L1 and the dialysate drain line L2, respectively, dialysate supply lines L3 and L4, a heating device h, a control device 9, and an outside-air-introducing device 10. Elements that are the same as those described in the first embodiment are denoted by corresponding ones of the reference numerals, and description of those elements is omitted.

The outside-air-introducing device 10 according to the second embodiment includes a pump device 10a (an air pump) attached to an extension flow route Lb extending from the dialysate introduction line L1 and whose distal end is open to the atmosphere. When the pump device 10a is activated, the outside air can be introduced into the dialysate introduction line L1 through the extension flow route Lb. The pump device 10a is a peristaltic pump that is capable of introducing the outside air or discharging the inside air by squeezing a flexible tube forming the flow route provided as the extension flow route Lb. If the dialysate is overheated by the heating device h, the outside air can be introduced into the dialysate introduction line L1 or the air in the dialysate introduction line L1 can be discharged in accordance with the dialysate that is caused to flow by the liquid delivery pump P2.

Figure 9:
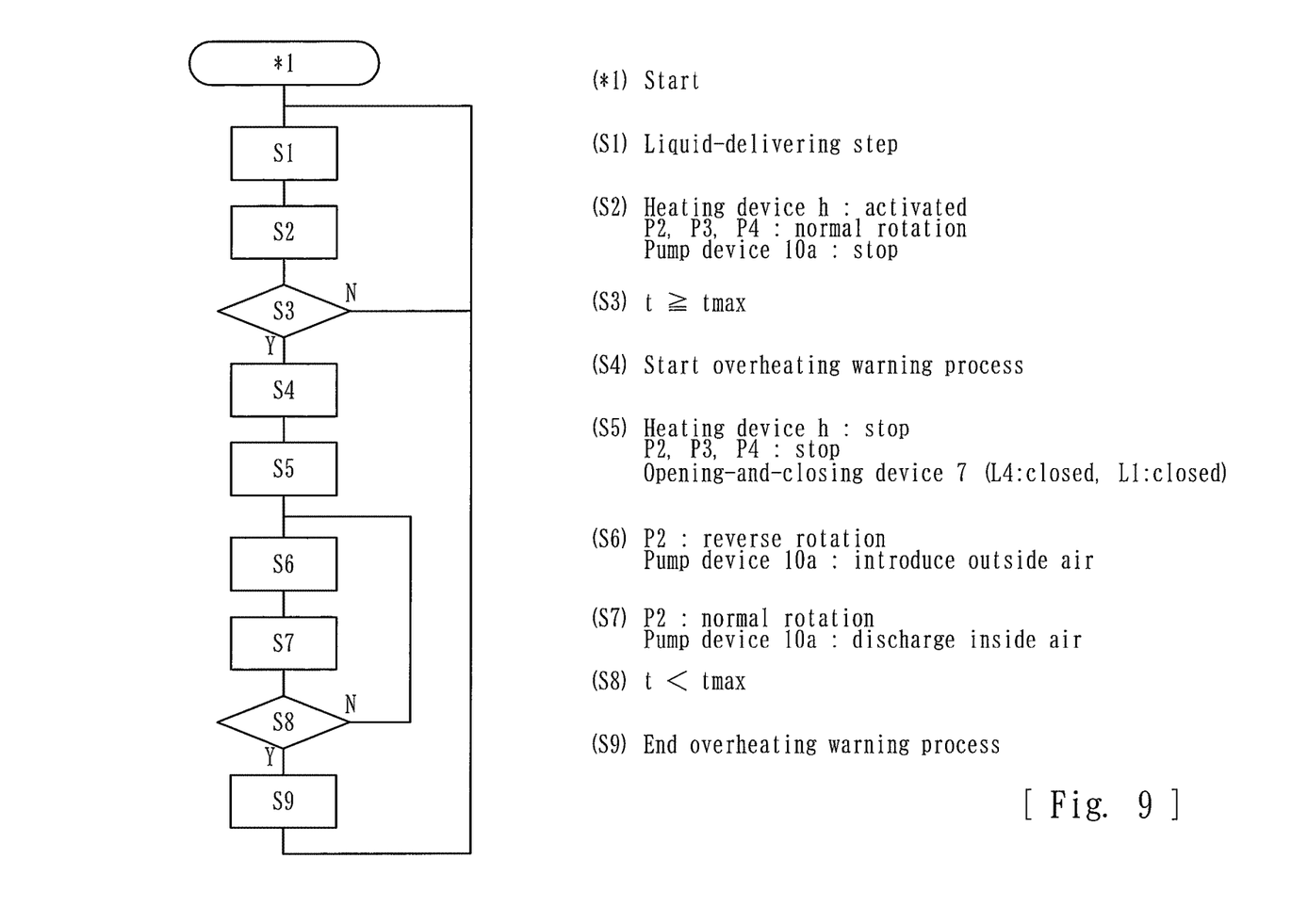
FIG. 9 is a flow chart of a control process executed by a control device included in the blood purification apparatus.

Now, a control process executed by the control device 9 according to the second embodiment will be described with reference to the flow chart illustrated in FIG. 9.

When a liquid-delivering step S1 of delivering the dialysate to the dialyzer 2 is started, the heating device h is activated and the liquid delivery pump P2, the filtration pump P3, and the peristaltic pump P4 are caused to undergo normal rotation in step S2. In this step, the pump device 10a is not in operation. Subsequently, whether or not a dialysate temperature t detected by the temperature-detecting devices T is higher than or equal to a predetermined temperature tmax (the predetermined value) is checked (in step S3). If the dialysate temperature t is lower than the predetermined temperature tmax, the liquid-delivering step S1 is continued.

If the dialysate temperature t detected by the temperature-detecting devices T is higher than or equal to the predetermined temperature tmax, the process proceeds to step S4, where an overheating warning process is started. Then, in step S5, the heating by the heating device h is stopped (the operation of the heat source is stopped), and the liquid delivery pump P2, the filtration pump P3, and the peristaltic pump P4 are also stopped. In this step, the opening-and-closing device 7 closes the dialysate supply line L4 and the flow route of the dialysate introduction line L1 that is on the side nearer to the dialyzer 2 than the heating device h. Since the peristaltic pump P4 is stopped, the dialysate supply line L3 is also closed. Thus, the introduction of the dialysate into the dialyzer 2 is stopped.

Subsequently, in step S6, the liquid delivery pump P2 is caused to undergo reverse rotation at a predetermined flow rate or for a predetermined period of time, whereby the dialysate in the heating device h (the dialysate in the flow route 8a of the heating bag 8) is caused to flow to the outside of the heating device h and toward the dialysate storage bag B1. Furthermore, the pump device 10a is activated (to undergo normal rotation), whereby the outside air is introduced into the dialysate introduction line L1. In this step, the dialysate in the heating device h only needs to reach the upstream portion of the dialysate introduction line L1. Preferably, the dialysate is caused to flow into the dialysate storage bag B1.

After the liquid delivery pump P2 is caused to undergo reverse rotation at a predetermined flow rate or for a predetermined period of time in step S6, the liquid delivery pump P2 is caused to undergo normal rotation in step S7, whereby the dialysate caused to flow in step S6 is returned into the heating device h (into the flow route 8a of the heating bag 8). In this step, the pump device 10a is activated (to undergo reverse rotation), whereby the air in the dialysate introduction line L1 (the outside air introduced in step S6) is discharged to the outside. Then, whether or not the dialysate temperature t detected by the temperature-detecting devices T is lower than the predetermined temperature tmax (the predetermined value) is checked (in step S8). If the dialysate temperature t is higher than or equal to the predetermined temperature tmax, the process returns to step S6, where the liquid delivery pump P2 is caused to undergo reverse rotation at a predetermined flow rate or for a predetermined period of time. Then, steps S7 and S8 are performed again. If the dialysate temperature t detected by the temperature-detecting devices T is lower than the predetermined temperature tmax, the process proceeds to step S9, where the overheating warning process is ended. Then, the control process is repeated from step S1.

The second embodiment employs the outside-air-introducing device 10. Furthermore, if the dialysate temperature detected by the temperature-detecting devices T is higher than or equal to the predetermined value, the outside-air-introducing device 10 allows the outside air to be introduced into the dialysate introduction line L1 in accordance with the dialysate that is caused to flow by the liquid delivery pump P2. Hence, even if the flow route is closed by the opening-and-closing device 7, the dialysate in the heating device h can be caused to flow to the outside of the heating device h assuredly and smoothly. In particular, the outside-air-introducing device 10 according to the second embodiment includes the pump device 10a attached to the extension flow route Lb extending from the dialysate introduction line L1 and whose distal end is open to the atmosphere. When the pump device 10a is activated, the outside air can be introduced into the dialysate introduction line L1 through the extension flow route Lb. Hence, the flow rate of the outside air to be introduced into the dialysate introduction line L1 can be adjusted as intended by controlling the driving of the pump device 10a. Thus, the level of the liquid in the air-trap chamber 5 can be adjusted on the basis of the result of detection by the liquid-surface-detecting sensor 6. Furthermore, the temperature-detecting devices T are preferably provide to the heating device h or to the flow route for introducing the dialysate heated by the heating device h into the dialyzer 2 (the blood purification device) or into the blood circuit 1. Thus, the temperature detection by the temperature-detecting devices T can be performed assuredly. Furthermore, the temperature of the dialysate can be lowered while the backward flow of the dialysate from the dialyzer 2 (the blood purification device) is prevented.

While some embodiments have been described above, the present teachings are not limited thereto. For example, if the dialysate temperature detected by the temperature-detecting devices T is higher than or equal to a predetermined value, the control device 9 may cause the liquid delivery pump P2 to undergo normal rotation so that the dialysate in the heating device h flows to a portion of the dialysate introduction line L1 that is on the downstream side (but on the upstream side with respect to the dialyzer 2). That is, the control device 9 only needs to cause the liquid delivery pump P2 to cause the dialysate in the heating device h to flow to a position on the upstream side or on the downstream side with respect to the heating device h, without allowing the dialysate to be introduced into the dialyzer 2 (the blood purification device). Alternatively, for example, a container that temporarily stores the dialysate so as to lower the temperature of the dialysate may be provided to a position of the dialysate introduction line L1 that is between the heating device h and the blood purification device 2. Moreover, elements such as the air-trap chamber 5 and the outside-air-introducing device (Y or 10) may be omitted. The blood purification treatment that is applicable is not limited to dialysis treatment and may be any other treatment for purifying the blood of a patient while extracorporeally circulating the blood.

The present teachings are applicable to any blood purification apparatus having any additional functions or the like, as long as the apparatus includes a control device configured such that, if the dialysate temperature detected by a temperature-detecting device is higher than or equal to a predetermined value, a liquid delivery pump is controlled to cause dialysate in a heating device to flow to a position on the upstream side or the downstream side with respect to the heating device without allowing the dialysate to be introduced into a blood purification device.

REFERENCE SIGN LIST 1 blood circuit
1a arterial blood circuit
1b venous blood circuit
2 dialyzer (blood purification device)
3 air-trap chamber
4 weighing machine
5 air-trap chamber
6 liquid-surface-detecting sensor
7 opening-and-closing device
8 heating bag
9 control device
10 outside-air-introducing device
h heating device
L1 dialysate introduction line L2 dialysate drain line
L3 dialysate supply line
L4 dialysate supply line
P1 blood pump
P2 liquid delivery pump
P3 filtration pump

The invention claimed is:

1. A blood purification apparatus comprising:
a blood circuit including an arterial blood circuit and a venous blood circuit and that is capable of extracorporeally circulating blood of a patient from a distal end of the arterial blood circuit to a distal end of the venous blood circuit;
a blood purification device provided between the arterial blood circuit and the venous blood circuit of the blood circuit and that is capable of purifying the blood flowing in the blood circuit;
a dialysate introduction line for introducing dialysate into the blood purification device and a dialysate drain line for discharging drain liquid from the blood purification device;
a liquid delivery pump provided to the dialysate introduction line and that is capable of causing the dialysate in the dialysate introduction line to flow;
a heating device that is capable of heating the dialysate to be introduced from the dialysate introduction line into the blood purification device;
a temperature-detecting device that is capable of detecting a temperature of the dialysate heated by the heating device;
a control device that is capable of controlling at least the liquid delivery pump and the heating device; and
an outside-air-introducing device that is capable of introducing, if a dialysate temperature detacted by the temperature-detecting device is higher than or equal to a predetermined value, outside air into the dialysate introduction line in accordance with the dialysate that is caused to flow by the liquid delivery pump,
wherein the control device is configured so that, if the dialysate temperature detected by the temperature-detecting device is higher than or equal to the predetermined value, the liquid delivery pump is controlled to cause the dialysate in the heating device to flow to an upstream side or a downstream side with respect to the heating device without allowing the dialysate to be introduced into the blood purification device.

2. The blood purification apparatus according to claim 1, wherein the liquid delivery pump is a peristaltic pump that is capable of undergoing normal rotation and reverse rotation, and wherein the control device is configured so that, if the dialysate temperature detected by the temperature-detecting device is higher than or equal to the predetermined value, the liquid delivery pump is controlled to cause the dialysate in the heating device to flow to an upstream portion of the dialysate introduction line by undergoing reverse rotation.

3. The blood purification apparatus according to claim 1, wherein the dialysate introduction line is connected to a dialysate storage bag that stores the dialysate by a predetermined amount, and wherein the control device is configured such that, if the dialysate temperature detected by the temperature-detecting device is higher than or equal to the predetermined value, the liquid delivery pump is controlled to cause the dialysate in the heating device to flow into the dialysate storage bag.

4. The blood purification apparatus according to claim 1, further comprising: a flow route for introducing the dialysate heated by the heating device into the blood purification device or into the blood circuit; and an opening-and-closing device that is capable of opening and closing the flow route, wherein the control device controls the opening-and-closing device to close the flow route if the dialysate temperature detected by the temperature-detecting device is higher than or equal to the predetermined value.

5. The blood purification apparatus according to claim 1, wherein the outside-air-introducing device includes a valve device that is attached to an extension flow route extending from the dialysate introduction line and whose distal end is open to atmosphere, the valve device being capable of opening and closing the extension flow route, and wherein, when the valve device is open, outside air is allowed to be introduced into the dialysate introduction line through the extension flow route.

6. The blood purification apparatus according to claim 1, wherein the outside-air-introducing device includes a pump device that is attached to an extension flow route extending from the dialysate introduction line and whose distal end is open to atmosphere, and wherein, when the pump device is activated, outside air is allowed to be introduced into the dialysate introduction line through the extension flow route.

7. The blood purification apparatus according to claim 1, further comprising a filtration pump provided to the dialysate drain line and that is capable of causing the drain liquid in the dialysate drain line to flow, wherein the control device is configured so that, if the dialysate temperature detected by the temperature-detecting device is higher than or equal to the predetermined value, the filtration pump is controlled to rotate at substantially the same flow rate and in the same direction as the liquid delivery pump.

8. The blood purification apparatus according to claim 4, wherein the temperature-detecting device is provided to the heating device or to a flow route for introducing the dialysate heated by the heating device into the blood purification device or into the blood circuit.

9. The blood purification apparatus according to claim 1, wherein the temperature-detecting device is provided to the heating device, and wherein the control device is configured so that, if the dialysate temperature detected by the temperature-detecting device is higher than or equal to the predetermined value, the temperature-detecting device is controlled to detect the temperature after the liquid delivery pump causes the dialysate in the heating device to flow to an outside of the heating device and after the liquid delivery pump returns the thus flowed dialysate to the heating device.

10. The blood purification apparatus according to claim 9, wherein, until the temperature detected by the temperature-detecting device becomes lower than the predetermined value, the control device repeatedly executes a step of causing the dialysate in the heating device to flow to the outside of the heating device and a step of returning the thus flowed dialysate to the heating device.

* * * * *